(12) United States Patent
Tanner

(10) Patent No.: US 8,573,147 B1
(45) Date of Patent: Nov. 5, 2013

(54) PIPE DIRECTION AND SIZE INDICATOR

(76) Inventor: Jeffrey M. Tanner, Zanesville, OH (US)

( * ) Notice: Subject to any disclaimer, the term of this patent is extended or adjusted under 35 U.S.C. 154(b) by 321 days.

(21) Appl. No.: 13/231,441

(22) Filed: Sep. 13, 2011

(51) Int. Cl.
  *G01N 21/954* (2006.01)
  *F16L 55/26* (2006.01)

(52) U.S. Cl.
  USPC ........... 116/200; 116/264; 116/273; 73/865.8

(58) Field of Classification Search
  USPC ............. 116/1, 200, 215, 264, 270, 273, 275, 116/278, DIG. 7; 73/49.1, 49.5, 865.8, 73/866.5; 119/708; 166/241.1, 241.6, 166/241.7; 254/134.3 FT; 348/82, 84, 85; 446/490; 976/DIG. 214
  See application file for complete search history.

(56) References Cited

U.S. PATENT DOCUMENTS

| | | | | |
|---|---|---|---|---|
| 498,351 | A | * | 5/1893 | Kasper ........................... 119/789 |
| 1,730,176 | A | * | 10/1929 | Thrasher et al. ............... 473/143 |
| 3,596,365 | A | | 8/1971 | Verhagen |
| 4,083,533 | A | * | 4/1978 | Schwabe ..................... 254/134.4 |
| 4,782,786 | A | | 11/1988 | Himmler |
| 5,467,640 | A | * | 11/1995 | Salinas ....................... 73/40.5 R |
| 5,901,667 | A | * | 5/1999 | Kallas ............................ 119/712 |
| 6,111,600 | A | * | 8/2000 | McLeod et al. ................... 348/84 |
| 6,697,102 | B1 | | 2/2004 | Olsson et al. |
| 6,743,072 | B2 | * | 6/2004 | Nelson et al. .................. 446/490 |
| 6,862,945 | B2 | | 3/2005 | Chapman et al. |
| 6,948,258 | B2 | * | 9/2005 | Coulombe ........................ 33/542 |
| 7,025,333 | B1 | * | 4/2006 | Gianturco ............ 254/134.3 FT |
| 7,259,842 | B2 | | 8/2007 | Erne et al. |
| 8,371,249 | B1 | * | 2/2013 | Little ............................ 119/708 |
| 2004/0021099 | A1 | | 2/2004 | Figueria et al. |
| 2012/0300057 | A1 | * | 11/2012 | Bartucciotto ..................... 348/84 |
| 2013/0081449 | A1 | * | 4/2013 | Li et al. ....................... 73/40.5 R |

FOREIGN PATENT DOCUMENTS

| | | | | | |
|---|---|---|---|---|---|
| CA | | 2402295 | A1 | * | 3/2004 ............... G01B 5/12 |
| JP | | 06098213 | A | * | 4/1994 ............. H04N 5/225 |
| JP | | 2008028722 | A | * | 2/2008 ............. H04N 5/225 |

* cited by examiner

*Primary Examiner* — R. A. Smith
(74) *Attorney, Agent, or Firm* — Jason L. Gilbert

(57) ABSTRACT

A pipe direction and size indicator which may be attached to a pipe inspection camera for use in determining the flow direction and size of a pipe. The pipe direction and size indicator generally includes an adapter member, extension member and indicator member. The adapter member is adapted to be removably attached to a camera. The extension member is removably secured to the adapter member by a threaded connection. The outer end of the extension member includes an indicator member which is attached thereto and allows the indicator member to freely rotate, swivel and move about the extension member. By observing the positioning of the indicator member, which will be freely affected by gravity, an operator of the present invention may determine the directional flow of a pipe being inspected. Further, by accounting for the size of the indicator member, the size of the pipe may also be determined.

18 Claims, 5 Drawing Sheets

PIPE DIRECTION AND SIZE INDICATOR

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to an indicator system and more specifically it relates to a pipe direction and size indicator which may be attached to a pipe inspection camera for use in determining the flow direction and size of a pipe.

2. Description of the Related Art

Any discussion of the related art throughout the specification should in no way be considered as an admission that such related art is widely known or forms part of common general knowledge in the field.

Pipes such as underground utility pipes will often require service on a regular basis to line the pipe, fix defects and the like. When inspecting or servicing such pipes, it is important to know the flow direction and size of the pipe being inspected or serviced. While pipe inspection cameras are commonly used, it is easy to lose track of the pipe direction when utilizing such cameras.

There are existing self-leveling lenses which may be utilized to show the bottom of the pipe being inspected. While these types of systems show the flow direction of gravity piping where fluid ruins in the bottom part of the pipe, these systems do not indicate flow direction for pressure piping and other non-gravity piping systems. With such systems, it is very difficult for the camera operator to tell which direction the pipes flow in, even with a self-leveling lens.

Because of the inherent problems with the related art, there is a need for a new and improved pipe direction and size indicator which may be attached to a pipe inspection camera for use in determining the flow direction and size of a pipe.

BRIEF SUMMARY OF THE INVENTION

The invention generally relates to a pipe direction and size indicator which includes an adapter member, extension member and indicator member. The adapter member is adapted to be securely and removably attached to a camera. The extension member is removably secured to the adapter member by a threaded connection. The outer end of the extension member will generally include an indicator member which is attached thereto in a manner which allows the indicator member to freely rotate, swivel and move about the extension member. By observing the positioning of the indicator member, which will be freely affected by gravity, an operator of the present invention may determine the directional flow of a pipe being inspected. Further, by accounting for the size of the indicator member, the size of the pipe may also be determined.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
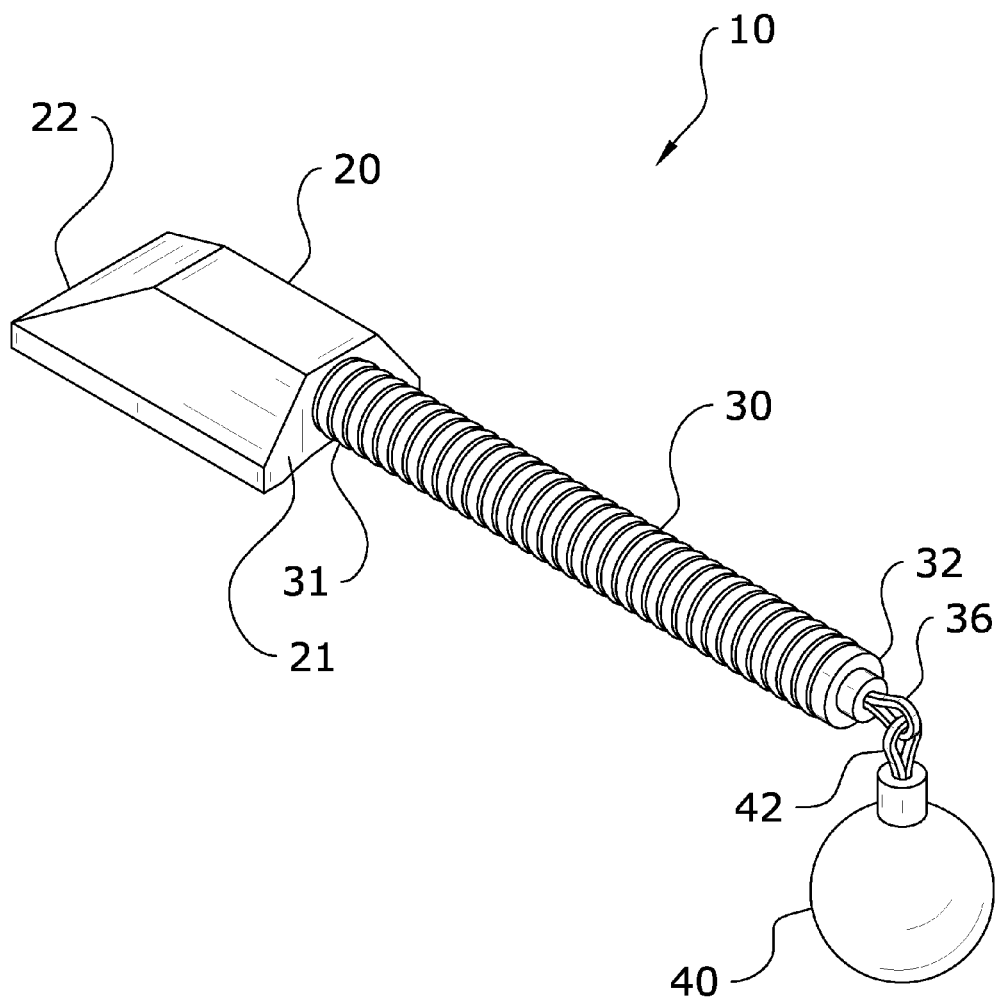
FIG. 1 is an upper perspective view of the present invention.

Turning now descriptively to the drawings, in which similar reference characters denote similar elements throughout the several views, FIGS. 1 through 6 illustrate a pipe direction and size indicator 10, which comprises an adapter member 20, extension member 30 and indicator member 40. The adapter member 20 is adapted to be securely and removably attached to a camera 12. The extension member 30 is removably secured to the adapter member 20 by a threaded connection. The outer end 32 of the extension member 30 will generally include an indicator member 40 which is attached thereto in a manner which allows the indicator member 40 to freely rotate, swivel and move about the extension member 30. By observing the positioning of the indicator member 40, which will be freely affected by gravity, an operator of the present invention may determine the directional flow of a pipe being inspected. Further, by accounting for the size of the indicator member 40, the size of the pipe may also be determined.

B. Adapter Member

The present invention will generally include an adapter member 20 for removably securing the present invention to a camera 12. The adapter member 20 of the present invention may be comprised of various shapes and sizes, and thus should not be construed as being limited to the specific structure shown in the figures As shown in FIG. 1, the adapter member 20 will generally include a front end 21 and a rear end 22. The front end 21 of the adapter member 20 will generally include an opening 24 which is adapted to receive the connection member 34 of the second end 32 of the extension member 30. The rear end 22 of the adapter member 22 is generally secured to a camera 12. In a preferred embodiment, the opening 24 of the front end 21 of the adapter member 20 will be threaded so that the connection member 34 of the extension member 30 may be threadably secured therein.

In a preferred embodiment, the adapter member 20 will include a flat upper surface with tapered side portions extending downwardly therefrom as shown in the figures to allow the adapter member 20 to be more firmly secured to a camera 12 when the present invention is in use. Further, a preferred embodiment will include a flat or slightly curved bottom surface which matches the contour of the camera 12 on which the present invention will be mounted.

C. Extension Member

Figure 2:
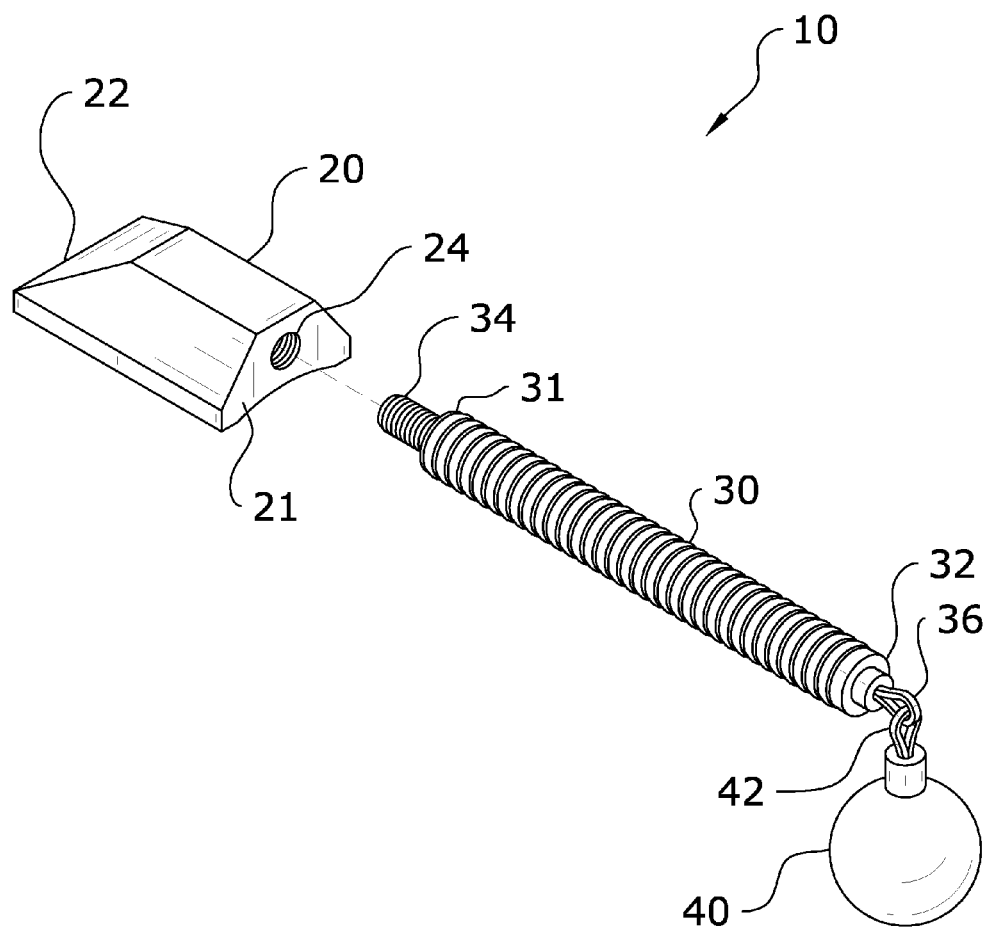
FIG. 2 is an upper perspective view of the present invention with the extension member separated from the adapter member.
Figure 3:
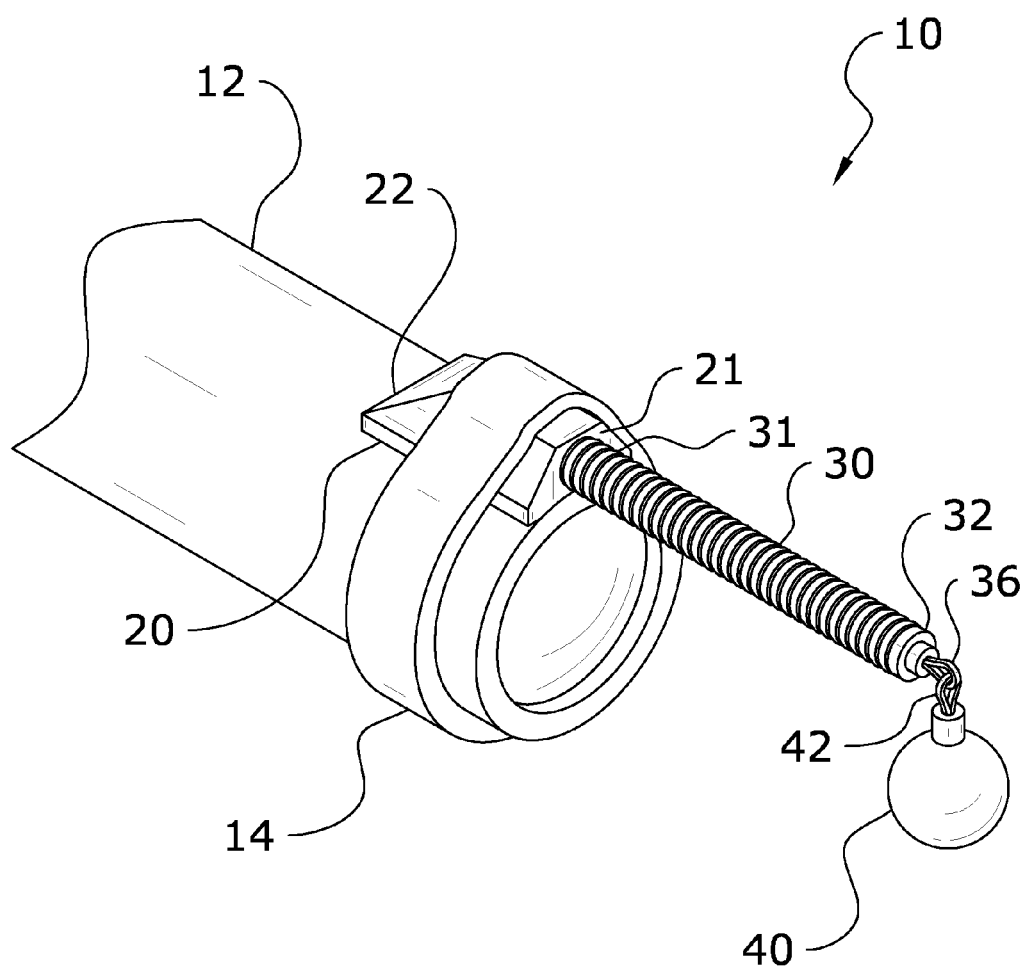
FIG. 3 is an upper perspective view of the present invention installed on a camera.
Figure 4:
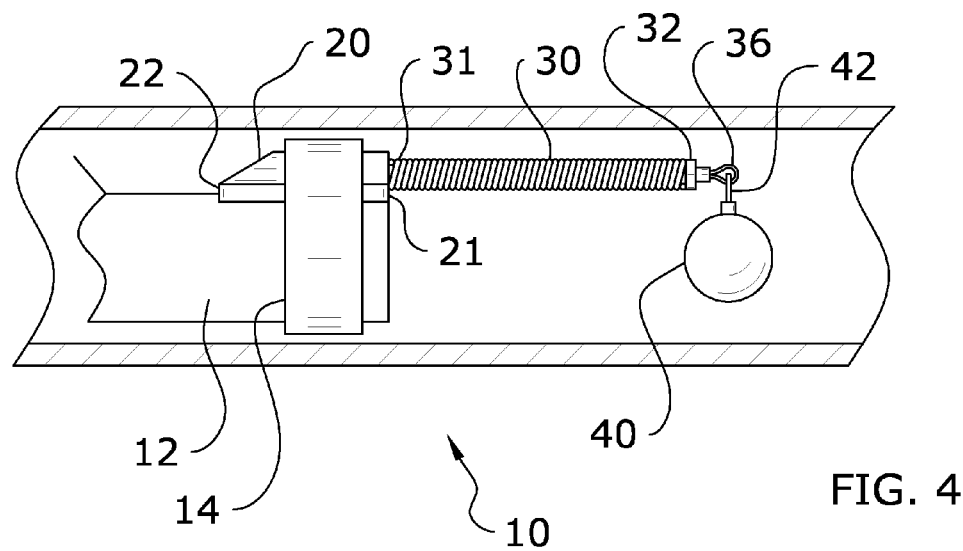
FIG. 4 is a first side view of the present invention in use.
Figure 5:
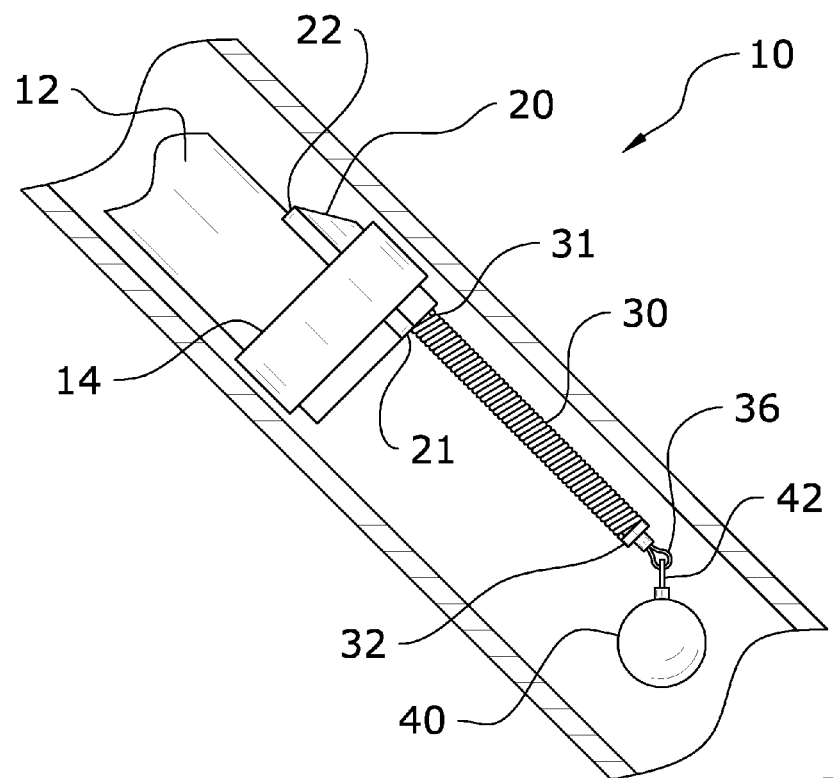
FIG. 5 is a second side view of the present invention in use.
Figure 6:
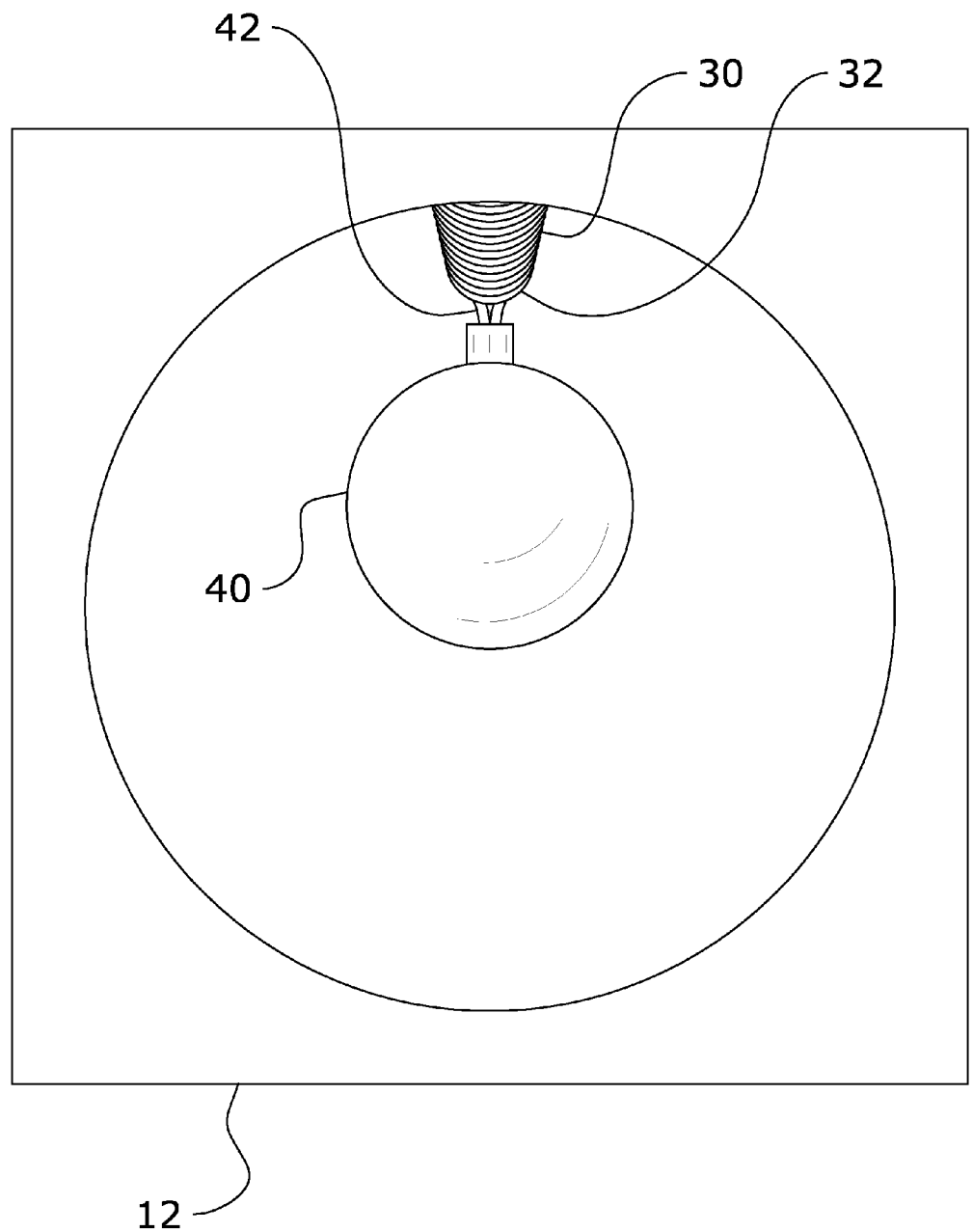
FIG. 6 is a front view of the present invention in use on a camera.

The present invention will also generally include an extension member 30 as shown in FIG. 2. The extension member 30 is utilized to ensure the indicator member 40 of the present invention is positioned a sufficient distance from the front of the camera 12 lens to ensure a proper reading.

As shown in FIG. 1, the extension member 30 will generally be comprised of an elongated member which may be removably attached to the front end 21 of the adapter member 20, which may then be secured to a camera 12. It is appreciated that, in some embodiments, the adapter member 20 may be omitted and the extension member 30 secured directly to the camera 12.

The extension member 30 may be comprised of various types of material. The extension member 30 will preferably be semi-rigid or flexible. In a preferred embodiment the extension member 30 will be comprised of an elongated, flexible spring. The extension member 30 includes a first end 31 and a second end 32, wherein the first end 31 is removably secured to the adapter member 20 of the present. The indicator member 40 of the present invention will generally be secured to the second end 32 of the extension member 30.

The first end 31 of the extension member 30 will generally include a connection member 34 for securely and removably attaching the extension member 30 to the adapter member 20 of the present invention. In a preferred embodiment, the connection member 34 will be comprised of a threaded male connector to threadably connect to the threaded opening 24 of the front end 21 of the adapter member 20.

The second end 32 of the extension member 30 will generally include a swivel member 36 on which the indicator member 40 of the present invention will be attached. The swivel member 36 may be comprised of various structures. In one embodiment shown in the figures, the swivel member 36 will be comprised of a loop structure which interacts with a matching loop structure on the indicator member 40 to allow the indicator member 40 to freely swivel, rotate and move in 360 degrees with respect to the extension member 30.

D. Indicator Member

The present invention will generally include an indicator member 40 to ease determination of pipe flow direction and size. The indicator member 40 will generally be comprised of a spherical structure which is attached to the second end 32 of the extension member 30 in a manner which allows the indicator member 40 to freely rotate and swivel. The diameter of the indicator member 40 may vary, but will preferably be comprised of a set value such as one inch to assist in sizing the pipe the indicator member 40 is positioned within.

The indicator member 40 will generally include an attachment member 42 for movably securing the indicator member 40 to the extension member 30. The attachment member 42 may be comprised of various structures, but will preferably be comprised of a structure which may be secured to the swivel member 36 of the extension member 30 to allow the indicator member 40 to freely rotate and swivel in response to the force of gravity. In a preferred embodiment, the attachment member 42 will be comprised of a loop structure which links with the loop structure of the connection member 34.

E. Operation of Preferred Embodiment

In use, the extension member 30 is first secured to the adapter member 20. The connection member 34 of the first end 31 of the extension member 30 is matingly engaged with the threaded opening 24 of the front end 21 of the adapter member 20 as shown in FIG. 2.

After securing the extension member 30 to the adapter member 20, the adapter member 20 may be secured to the camera 12. Generally, a mounting member 14 will be provided for removably securing the adapter member 20 to the camera 12. The mounting member 14 may be comprised of various structures which allow a secure but removable connection. In a preferred embodiment, tape may be utilized as a mounting member 14.

With the present invention secured to a camera 12, the camera 12 may be inserted within the pipe for inspection. Gravity will cause the indicator member 40 to always hang downwards, which will assist in flow direction determination. Further, the preset size of the indicator member 40 may be utilized to determine the size of the pipe being inspected.

When inspection is completed, the adapter member 20 may be removed from the camera 12 and the extension member 30 may be removed from the adapter member 20 to be stored for further use.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A pipe direction and size indication device, comprising:
    an adapter member adapted to be removably secured to a camera;
    an extension member connected to said adapter member; and
    an indicator member connected to said extension member for use in determining the size and directional flow of a pipe, wherein said indicator member is connected in a manner which allows said indicator member to freely rotate and swivel about said extension member.

2. The pipe direction and size indication device of claim 1, wherein said adapter member includes a front end and a rear end, wherein said front end of said adapter includes an opening.

3. The pipe direction and size indication device of claim 2, wherein said opening is threaded.

4. The pipe direction and size indication device of claim 3, wherein said extension member includes a first end and a second end, wherein said first end of said extension member includes a connection member.

5. The pipe direction and size indication device of claim 4, wherein said connection member is threaded.

6. The pipe direction and size indication device of claim 1, wherein said extension member is comprised of a flexible material.

7. The pipe direction and size indication device of claim 6, wherein said extension member is comprised of an elongated spring.

8. The pipe direction and size indication device of claim 1, wherein said extension member includes a swivel member.

9. The pipe direction and size indication device of claim 8, wherein said indicator member includes an attachment member.

10. The pipe direction and size indication device of claim 9, wherein said swivel member of said extension member is attached to said attachment member of said indicator member.

11. The pipe direction and size indication device of claim 1, wherein said indicator member is comprised of a spherical shape.

12. The pipe direction and size indication device of claim 11, wherein said indicator member has a diameter of one inch.

13. A pipe direction and size indication device, comprising:
- an adapter member adapted to be removably secured to a camera, wherein said adapter member includes a front end and a rear end;
- an opening positioned on said front end of said adapter member;
- an extension member, wherein said extension member includes a first end and a second end, wherein said first end of said extension member is connected to said front end of said adapter member; and
- an indicator member connected to said second end of said extension member for use in determining the size and directional flow of a pipe, wherein said indicator member is connected in a manner which allows said indicator member to freely rotate and swivel about said extension member.

14. The pipe direction and size indication device of claim 13, wherein said opening is threaded.

15. The pipe direction and size indication device of claim 13, wherein said extension member is comprised of an elongated, flexible material.

16. The pipe direction and size indication device of claim 13, wherein said extension member is comprised of an elongated spring.

17. The pipe direction and size indication device of claim 13, wherein said indicator member is comprised of a spherical shape.

18. A pipe direction and size indication system, comprising:
- a camera;
- an adapter member adapted to be removably secured to said camera, wherein said adapter member includes a front end and a rear end;
- a mounting member for securing said adapter member to said camera, wherein said mounting member is comprised of tape;
- a threaded opening positioned on said front end of said adapter member;
- an extension member, wherein said extension member includes a first end and a second end, wherein said first end of said extension member includes a threaded connection member, wherein said threaded connection member is adapted to matingly engage with said threaded opening; and
- an indicator member connected to said second end of said extension member for use in determining the size and directional flow of a pipe, wherein said indicator member is connected in a manner which allows said indicator member to freely rotate and swivel about said extension member, wherein said indicator member is comprised of a spherical shape.

\* \* \* \* \*